United States Patent
Mark et al.

(10) Patent No.: US 12,369,936 B2
(45) Date of Patent: Jul. 29, 2025

(54) IN-PLANE ROTATION CANNULA

(71) Applicant: NICO CORPORATION, Indianapolis, IN (US)

(72) Inventors: Joseph L. Mark, Indianapolis, IN (US); Brian C. Dougherty, Terra Haute, IN (US)

(73) Assignee: Stryker Corporation, Portage, MI (US)

( * ) Notice: Subject to any disclaimer, the term of this patent is extended or adjusted under 35 U.S.C. 154(b) by 118 days.

(21) Appl. No.: 17/766,991

(22) PCT Filed: Oct. 6, 2020

(86) PCT No.: PCT/US2020/054407
§ 371 (c)(1),
(2) Date: Apr. 6, 2022

(87) PCT Pub. No.: WO2021/071840
PCT Pub. Date: Apr. 15, 2021

(65) Prior Publication Data
US 2024/0074779 A1    Mar. 7, 2024

Related U.S. Application Data

(60) Provisional application No. 62/911,762, filed on Oct. 7, 2019.

(51) Int. Cl.
*A61B 17/32* (2006.01)
*A61B 10/02* (2006.01)

(52) U.S. Cl.
CPC .... *A61B 17/32002* (2013.01); *A61B 10/0275* (2013.01); *A61B 10/0283* (2013.01);
(Continued)

(58) Field of Classification Search
CPC .......... A61B 17/32002; A61B 10/0275; A61B 10/0283; A61B 2017/320028;
(Continued)

(56) References Cited

U.S. PATENT DOCUMENTS 5,669,926 A    9/1997  Aust et al.
9,078,639 B2 *  7/2015  Landrigan ............ A61B 10/025
(Continued)

FOREIGN PATENT DOCUMENTS

JP    2001517474 A    10/2001
JP    2012504432 A    2/2012
(Continued)

OTHER PUBLICATIONS

International Search Report for Application No. PCT/US2020/054407 dated Jan. 11, 2021, 1 page.

*Primary Examiner* — Tan-Uyen T Ho
*Assistant Examiner* — Khoa Tan Le
(74) *Attorney, Agent, or Firm* — Howard & Howard Attorneys PLLC

(57) ABSTRACT

A tissue cutting device is disclosed that allows for in-plane rotation of a distal end to avoid gross movements during surgical procedures. In one exemplary arrangement, the tissue cutting device comprises a housing, an outer cannula, and an inner cannula. The outer cannula is mounted for rotation to the handpiece. The inner cannula is mounted within the outer cannula and mounted for rotation with the outer cannula. Both the inner and outer cannula are provided with relieving cuts that are offset from one another.

20 Claims, 4 Drawing Sheets

(52) U.S. Cl.
CPC ............. *A61B 2017/320028* (2013.01); *A61B 2017/320032* (2013.01)

(58) Field of Classification Search
CPC . A61B 2017/320032; A61B 17/320016; A61F 9/00763
See application file for complete search history.

(56) References Cited

U.S. PATENT DOCUMENTS

| | | |
|---|---|---|
| 9,186,175 B2 | 11/2015 | Mark et al. |
| 9,387,010 B2 | 7/2016 | Mark et al. |
| 10,368,890 B2 | 8/2019 | Mark |
| 2004/0087831 A1* | 5/2004 | Michels ............. A61B 17/3415 600/114 |
| 2007/0032741 A1 | 2/2007 | Hibner et al. |
| 2012/0078279 A1* | 3/2012 | Mark ................. A61B 10/0275 606/171 |
| 2012/0136277 A1 | 5/2012 | Landrigan et al. |
| 2013/0035609 A1 | 2/2013 | Darr |
| 2014/0135779 A1* | 5/2014 | Germain ............ A61B 17/1642 606/93 |
| 2015/0359595 A1 | 12/2015 | Ben Oren et al. |
| 2019/0021754 A1* | 1/2019 | Dougherty et al. ........................ A61B 10/0275 |

FOREIGN PATENT DOCUMENTS

| | | |
|---|---|---|
| JP | 2012525915 A | 10/2012 |
| JP | 2012527918 A | 11/2012 |
| JP | 2019517854 A | 6/2019 |

* cited by examiner

IN-PLANE ROTATION CANNULA

CROSS-REFERENCE TO RELATED APPLICATIONS

This application is the U.S. National Phase of PCT Application No. PCT/US2020/054407 filed on Oct. 6, 2020, which claims the benefit of U.S. provisional application Ser. No. 62/911,762 filed Oct. 7, 2019, the disclosures of which are hereby incorporated in their entirety by reference herein.

TECHNICAL FIELD

The present disclosure relates generally to a cannula arrangement for a surgical device and more particularly to a cannula arrangement that may be selectively bent, but still allows for 360 degrees of rotation within the same plane after the bend point.

BACKGROUND

Advances in surgical techniques and devices have allowed for access to deep seated tumors that were previous though to be inaccessible. More specifically, narrow surgical corridors allow for such access to the structures.

However, often it is difficult to differentiate between normal and abnormal tissue, and many known surgical devices have line of sight issues whereby the shaft and/or the effector end of the instrument is very difficult to observe during a procedure without also occluding the surgeon's view of the surgical site due to the narrow surgical corridor. As a result, users are often required to hold the instrument at awkward angles so as to maintain visibility during the procedure, which may lead to unintended movements by the operator causing harm to normal tissues.

Further, because of the size and angle at which the instrument must be entered into the surgical site, the actual use of the instrument may block the surgeon's view of the surgical site during its use and the surgeon effectively uses the instrument "blindly" and removes the instrument from the surgical field to inspect the outcome of the use of the instrument. If unsatisfactory, then the instrument is then repositioned in the surgical field for additional work. This procedure can often go on for multiple passes at the surgical site. Such repeated action can cause damage to the tissues which line the surgical corridor due to bumping of the instrument as they are passed in and out, as well as unintentional excision of healthy tissue. Accordingly, this results in procedural inefficiency as well as increased surgeon fatigue.

Manipulation of the surgical device is also difficult within the surgical field. For example, while a device may be configured to cut tissue or grasp different structures, often there is no mechanism to change angles of orientation of the effector end of the device during the cutting or grasping operation while it is in use within the surgical site. Accordingly, the user has traditionally been required to extract the device from the surgical field to reposition the device for further operation or remove the device and angle a lighting device to provide sufficient visibility. This action thus lengthens a procedure. Moreover, depending on the set up in the operating suite, in some instances the repositioned angle requires the user to hold and operate the device in an awkward manner, also leading to fatigue and an unintended adverse impact to the tissues within the surgical site.

In other arrangements, while the end effector may be rotated while within the surgical site, if those arrangements are bent to allow for effective line of sight during use of the device, rotation of the end effector results in a gross arc movement, moving a tissue opening dramatically. For operations being performed within the surgical access corridor, such movement is often prohibitive as the end effector swings into the walls of the surgical access corridor. Further such movement also results in requiring a surgeon to physically move their hand, wrist, or even arm to properly reposition the tissue opening to a location where the effective portion of the device is visible and can access the desired area.

Based on the foregoing, an improved device that allows for easy manipulation for both line of sight issues, as well as to permit flexibility of use during a procedure is needed, while minimizing gross movement of the device.

BRIEF SUMMARY OF THE INVENTION

A surgical device is disclosed that allows for in-plane rotation of a distal end to avoid gross movements during surgical procedures. In one exemplary arrangement, the surgical device comprises a housing, an outer cannula, and an inner cannula. The outer cannula is mounted for rotation to the handpiece. The inner cannula is mounted within the outer cannula and mounted for rotation with the outer cannula.

To allow for in-plane rotation, the outer cannula includes a plurality of outer relieving cuts disposed thereon. Similarly, the inner cannula includes a plurality of inner relieving cuts disposed thereon. The outer relieving cuts are offset from the inner relieving cuts such that the outer relieving cuts do not overlap with the inner relieving cuts when the inner and outer cannulas are in a first position.

In a further embodiment, the surgical device further comprises a vacuum sleeve mounted to the outer cannula, the vacuum sleeve being disposed over the outer relieving cuts to maintain vacuum within the surgical device.

In a further embodiment, the surgical device further comprises a stiffening sleeve disposed over the outer cannula.

BRIEF DESCRIPTION OF THE DRAWINGS

Exemplary embodiments of the present disclosure will now be described in greater detail with reference to the attached figures, in which.

DETAILED DESCRIPTION OF THE INVENTION

Figure 1:
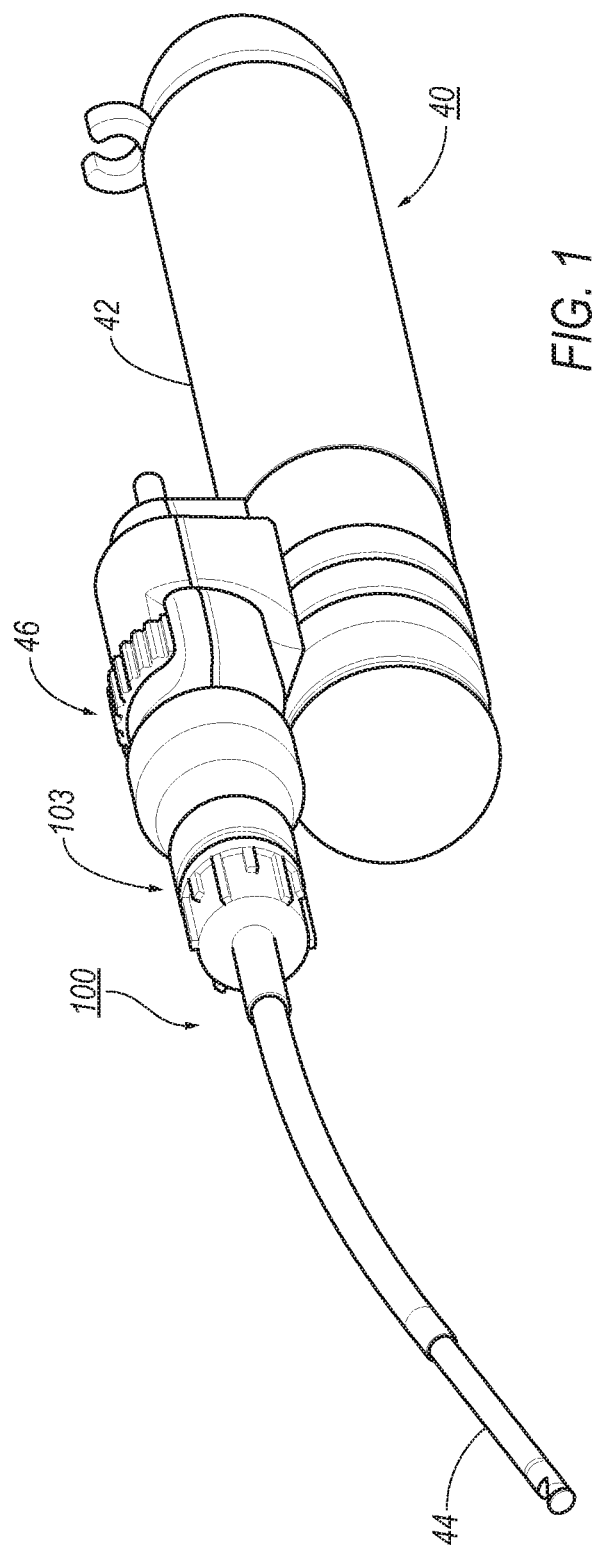
FIG. 1 is a perspective view of a surgical device with a stiffening adapter mounted thereto.

Referring now to the discussion that follows and also to the drawings, illustrative approaches to the disclosed assemblies and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein are surgical devices that are suited for neurosurgical applications such as the removal of spine and brain tissue. The components disclosed herein provide surgeons with an enhanced ability to minimize trauma to the patient, while providing efficient improved minimally invasive surgical techniques, such as, for example, during intracranial surgical techniques. The components disclosed herein may further be used for application of targeted and effective treatment regimens. Referring to FIG. 1, an exemplary surgical device 40 is shown. In one exemplary arrangement, the surgical device may be configured as a tissue cutting device. More specifically, surgical device 40 may be configured similarly to the shown and described in commonly owned U.S. Pat. No. 9,387,010, the contents of which are incorporated in its entirety.

In one exemplary arrangement, surgical device 40 includes a handpiece 42 and an outer cannula 44. A rotation dial 46 for selectively rotating the outer cannula 44 with respect to handpiece 42 is mounted within a portion of handpiece 42.

Figure 4:
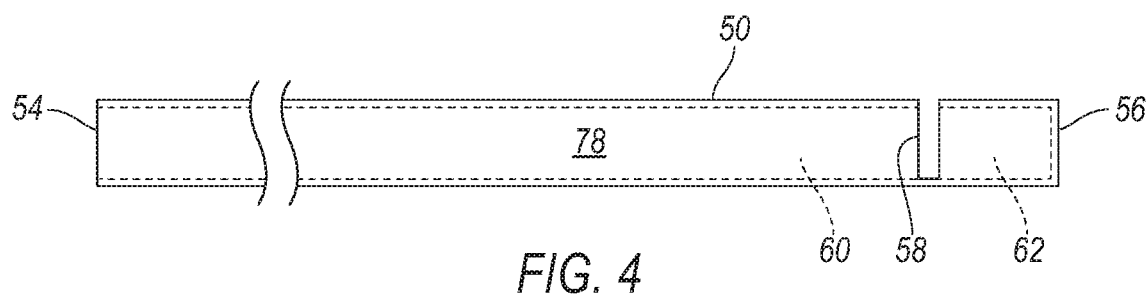
FIG. 4 is a side elevational view of a prior art inner cannula of a tissue cutting device.
Figure 5A:
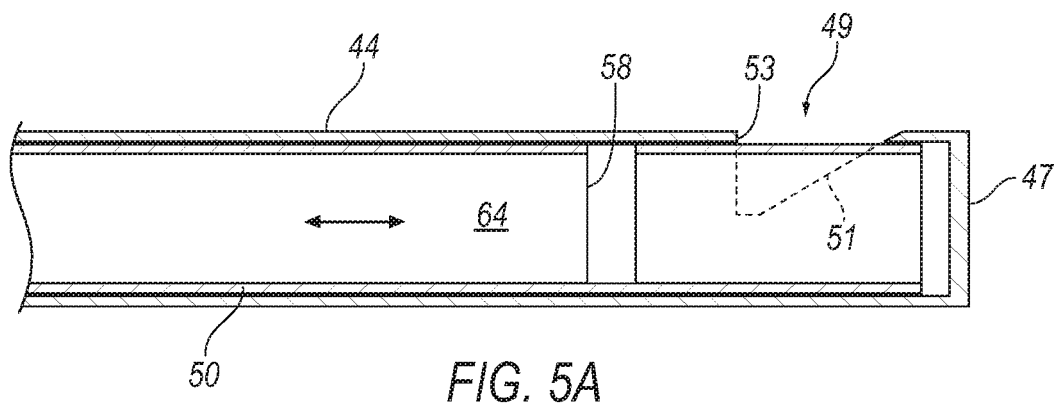
FIG. 5A is a cross-sectional view of a prior art assembled inner and outer cannula of a tissue cutting device in a cutting position.
Figure 5B:
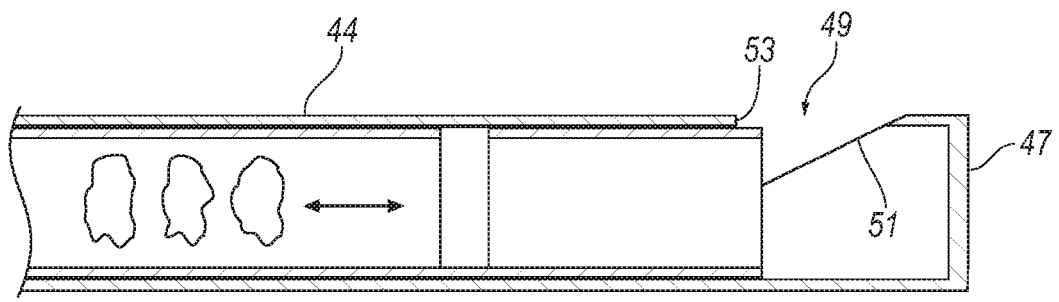
FIG. 5B is a cross-section view of the prior art assembled inner and outer cannula of the tissue cutting device in retracted position.

As best seen in FIGS. 3-5B, prior art outer cannula 44 includes an open proximal end 45, a closed distal end 47, and a distal opening 49 proximate distal end 47. Surgical device 40 further comprises an inner cannula 50 which is partially disposed in an outer cannula lumen 52. In one exemplary arrangement, inner cannula 50 is configured to reciprocate within outer cannula lumen 52 and to cut tissue samples entering outer cannula 44 via outer cannula distal opening 49. Inner cannula 50 reciprocates between a proximal position and a distal position. Referring to FIG. 4, inner cannula 50 includes an open proximal end 54 and an open distal end 56. Distal end 56 is configured to cut tissue, and in certain exemplary arrangements is configured for cutting neurological system tissues such as those from the brain or spine. In another exemplary arrangement, inner cannula 50 is used to selectively deliver vacuum to a surgical site such that movement of the inner cannula 50 to a distal position reduces and/or prevents vacuum from being delivered to the tissue opening 49.

Outer cannula 44 is not translatable, and its position with respect to handpiece 42 along the direction of the longitudinal axis of handpiece 42 remains fixed. A motor (not shown) is disposed in a section of handpiece 42 and is operably connected to inner cannula 50 to drive the reciprocation of inner cannula 50 within outer cannula lumen 52.

Outer cannula 44 includes an opening 49 for receiving tissue into outer cannula lumen Opening 49 may be defined by a cutting edge 51 that is configured to sever tissue and a non-cutting edge 53 that is not configured to sever tissue. In one embodiment, inner cannula distal end 56 is preferably configured to cut tissue. As tissue is received in outer cannula opening 49, it is compressed between inner cannula distal end 56 and outer cannula cutting edge 51, causing the received tissue to be severed from the surrounding tissue.

Inner cannula may include a hinge 58. Hinge 58 is located between an inner cannula body section 60 which is located on the proximal side of hinge 58 and inner cannula cutting section 62 which is located on the distal side of hinge 58. Hinge 58 allows cutting section 62 to pivot about hinge 58 as inner cannula 50 reciprocates within outer cannula 44. As inner cannula 50 translates in the distal direction, it contacts tissue received in outer cannula opening 49 and encounters progressively increasing resistance from the tissue as the tissue is urged in the distal direction. As the resisting force of the tissue increases, cutting section 62 pivots progressively more until a zero annular clearance is obtained between inner cannula distal end 56 and outer cannula opening 49. The received tissue is severed and aspirated in the proximal direction along inner cannula lumen 64 and is received in a tissue collector (not shown). Thus, inner cannula lumen 64 provides an aspiration path from the inner cannula distal end 56 to the inner cannula proximal end 54.

Surgical device 40 aspirates tissue samples received in inner cannula lumen 64 to cause the tissue samples to move in the proximal direction along the length of the inner cannula 50. In some exemplary embodiments, surgical device 40 preferably includes a tissue collector (not shown) into which aspirated tissue samples are deposited during a tissue cutting procedure. In some exemplary arrangements, the tissue collector may be located remotely from handpiece 42 and outside the sterile field during a tissue cutting operation or may be removably connected to handpiece 40.

When device 40 is used to cut tissue, outer cannula opening 49 must be aligned with the target tissue of interest to receive it for cutting. In an exemplary embodiment, device 40 includes a selectively rotatable outer cannula 44. As best seen in FIG. 1, a rotation dial 46 is provided and is rotatably seated within the handpiece 42. Rotation dial 46 is configured such that when it is rotated, it causes outer cannula 44 to rotate about its longitudinal axis.

To ensure the correct operation of hinge 58 of inner cannula 50, the circumferential alignment of hinge 58 and outer cannula opening 49 should be maintained. Thus, rotation dial 46 is preferably connected to inner cannula 50 such that when rotation dial 46 is rotated, both outer cannula 44 and inner cannula 50 rotate in a fixed angular orientation with respect to one another by an amount that directly corresponds to the amount by which rotation dial 46 is rotated. Rotation dial 46 may be directly connected to inner cannula 50 or may use an intervening connecting device. However, rotation dial 46 should be configured to allow inner cannula 50 to reciprocate with respect to rotation dial 46.

Because rotation dial 46 is directly or indirectly connected to both outer cannula 44 and inner cannula 50, both cannulae rotate in direct correspondence to the rotation of rotation dial 46, thereby allowing the user to adjust the orientation of outer cannula opening 49 and inner cannula hinge 58 in a circumferential direction with respect to handpiece 42. As a result, surgeons need not rotate the entire tissue cutting device 40 to obtain the desired angular orientation.

Rotation dial 46, outer cannula 44, and inner cannula 50 are preferably configured for 360° rotation. In addition, tactile indicators are preferably provided on rotation dial 46 to allow a user to reliably determine the extent to which dial 46 has been rotated from a given starting point. The tactile indication may comprise surface features defined on or in the exterior surface of rotation dial 46.

In one configuration, surgical device 40 is connected to a vacuum source and configured for variable aspiration, i.e., configured to supply variable levels of vacuum to inner cannula lumen 64.

Figure 2:
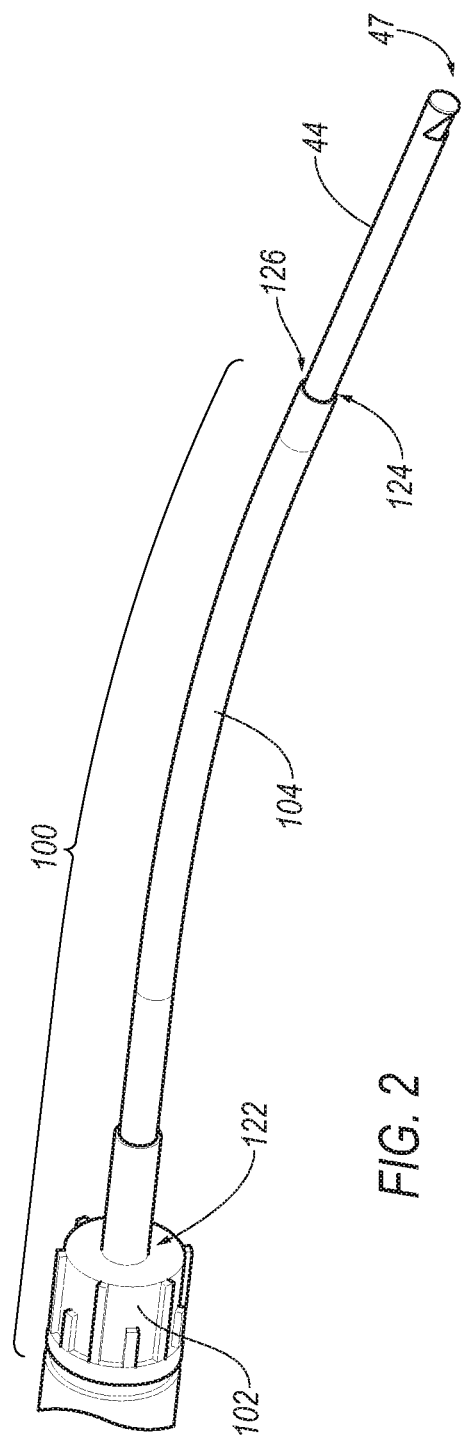
FIG. 2 is an enlarged view of the stiffening adapter disposed about an outer cannula of a surgical device.
Figure 3:
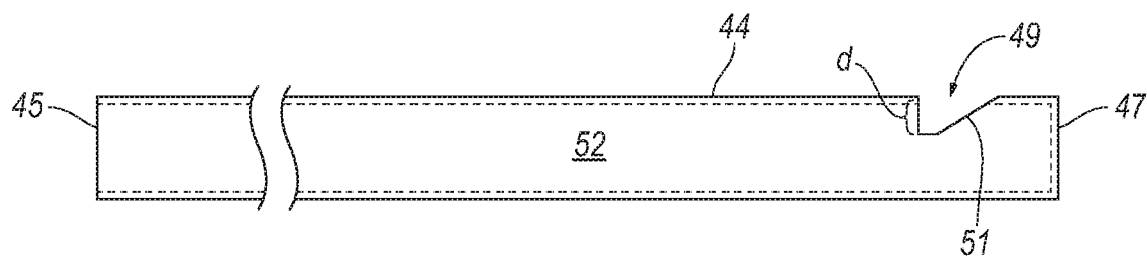
FIG. 3 is a side elevational view of a prior art outer cannula of a tissue cutting device.

Referring to FIGS. 1-2, a stiffening adapter 100 is illustrated that may be selectively attached to the surgical device 40. An exemplary stiffening adapter 100 is described in co-owned U.S. Pat. No. 10,383,680, the disclosure of which is incorporated by reference in its entirety. While tissue cutting deice 40 is depicted in FIG. 1, it is understood that stiffening adapter 100 may be used with other embodiments of surgical devices.

In one exemplary arrangement, stiffening adapter 100 comprises cap member 102 and a stiffening sleeve 104. In one exemplary arrangement, the stiffening adapter 100 is configured to be fixedly connected to the surgical device 40. Stiffening adapter 100 may be fixedly connected using glue, ultrasonic welding and/or a snap-fit arrangement, among other suitable attachment mechanisms. Once connected to the surgical device, the stiffening adapter 100 does not rotate.

Alternatively, the stiffening adapter 100 may be configured to be selectively detachable. For example, the cap member 102 may be threadingly engaged with the distal end 103 of the surgical device 40. In such an example, the interior of the cap member 102, as well as a portion of an outer surface of the distal end 103 of the tissue cutting device 40 would need to include corresponding threads. Other suitable methods of selectively attaching the stiffening adapter 100 to the tissue cutting device 40 include using a cooperating keyed connection or other mechanical attachment mechanism.

The stiffening sleeve 104 is defined by a proximal end 122 and a distal end 124. The proximal end 122 is mounted to the cap member 102. The stiffening sleeve 104 includes a channel 126 that extends between the proximal and distal ends 122 and 124. The diameter of the channel 126 is sized to be slightly larger than a cross-section dimension of outer cannula 44. The length of the stiffening sleeve 104 is sized to be shorter than the length of the outer cannula 44 so as to allow visibility of and access to the tissue opening 49.

The stiffening sleeve 104 is constructed of a material that is more rigid than the outer cannula 44. One example of a suitable material is stainless steel, though it is contemplated that other suitable materials may also be used.

In one exemplary arrangement the material for the stiffening sleeve may have a degree of malleability that allows a user to impart a bending force to achieve a desired bend in the stiffening sleeve that facilitates a line of sight to a working end of the surgical device 40, as discussed below. Once bent, the stiffening sleeve 104 will retain the shape of the bend once the bending force is removed. Alternatively, the stiffening sleeve 104 may be provided with a bend preformed. Providing a bend to direct the distal end 47 of the tissue cutting device 44 away from a longitudinal axis of the tissue cutting device 44 advantageously improves a line of sight for using the surgical device. This is especially true if the tissue cutting device is used in a delivery cannula, such as that disclosed in commonly owned U.S. patent application Ser. No. 13/444,713, the contents of which are incorporated by reference in its entirety.

The stiffening sleeve 104 may also be provided with an anti-reflective surface. In one exemplary arrangement, the anti-reflective surface may be formed by texturing all or part of the outer surface of the stiffening sleeve 104. The anti-reflective surface serves to prevent glare from illumination sources, thereby reducing eye fatigue during use of the surgical device 40.

Referring to FIGS. 6-10, details of the inner cannula 50' and outer cannula 44' that allow for in-plane rotation will now be described. In FIGS. 6-9, the stiffening adapter 100 is hidden for clarity.

As explained above, when the inner and outer cannula 50', 44' are rotated, it is important to minimize gross movement within the operating field. This is particularly true for devices that include a non-liner axis (i.e., a bend B) as the operational end (i.e., the distal end) will swing about the axis proximal of the bend point when rotated, such that the operation end swings out of plane along a large arc. To minimize such movement and allow the operational end to be rotated 360 degrees in plane after a bend point (i.e., about the axis distally of the bend point), the inner cannula 50' and the outer cannula 44' are provided with one or more relieving cuts 130 (outer cannula 44', best see in FIGS. 6-7) and 132 (inner cannula 50', best seen in FIGS. 8-9). Relieving cuts 130, 132 prevent interference between the inner and outer cannulas 50', 44' during rotation at the bend.

Figure 8:
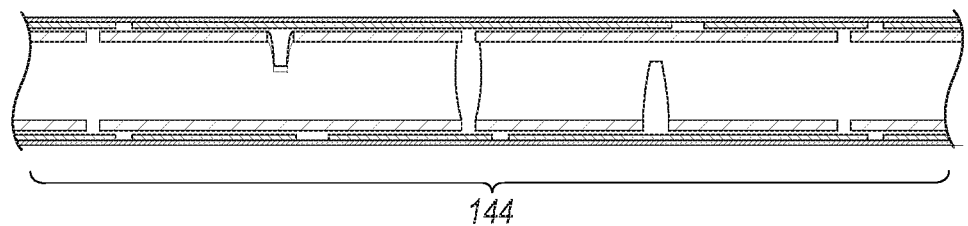
FIG. 8 is an enlarged cross-sectional view of a portion of the inner and outer cannula assembly of FIG. 6 when the surgical device is in a retracted position.
Figure 9:
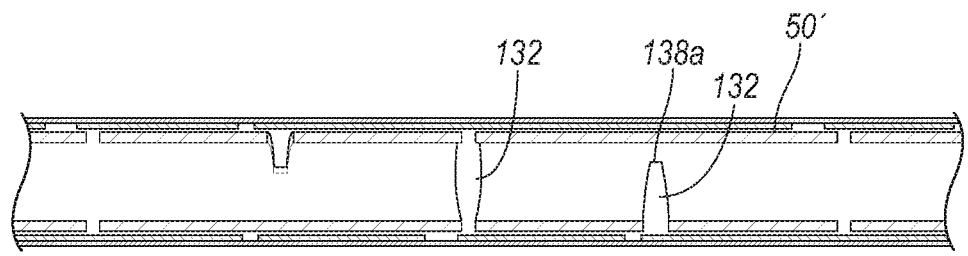
FIG. 9 is an enlarged cross-sectional view of a portion of the inner and outer cannula assembly when the surgical device is in a forward position.
Figure 10:
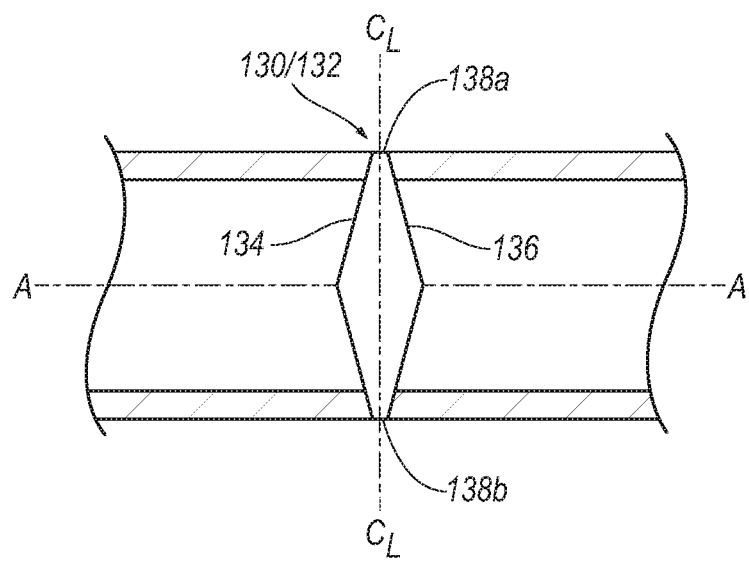
FIG. 10 is a plan view of an exemplary arrangement of a relieving cut.

Referring to FIG. 10, in one exemplary arrangement, relieving cuts 130/132 FIGS. 6-9, are formed with a diamond shape when viewed in plan. In one exemplary arrangement, the relieving cuts 130 are formed by removing a portion of a sidewall that forms the outer cannula 44'. A center line CL is disposed through the relieving cut 130/132, bisecting the relieving cut 130/132. A first side 134 of the relieving cut 130/132 is angled away from the center line CL until reaching a central axis A-A at which point first side 134 angles back inward toward center line CL. Similarly, a second side 136 of the relieving cut 130/132 is angled away from the center line CL until reaching central axis A-A, and then angles back inward toward the center line CL. In one exemplary arrangement, where the first and second sides 134/136 join together, a land area 138a, 138b may be formed.

The first and second sides 134/136 angles between 5-20 degrees from the centerline CL. In one exemplary arrangement, the first and second sides 134/136 extend 8 degrees from the centerline CL. The relieving cuts 130/132 serve to prevent interference at the bend point BP of the outer cannula 44' and inner cannula 50'.

Figure 6:
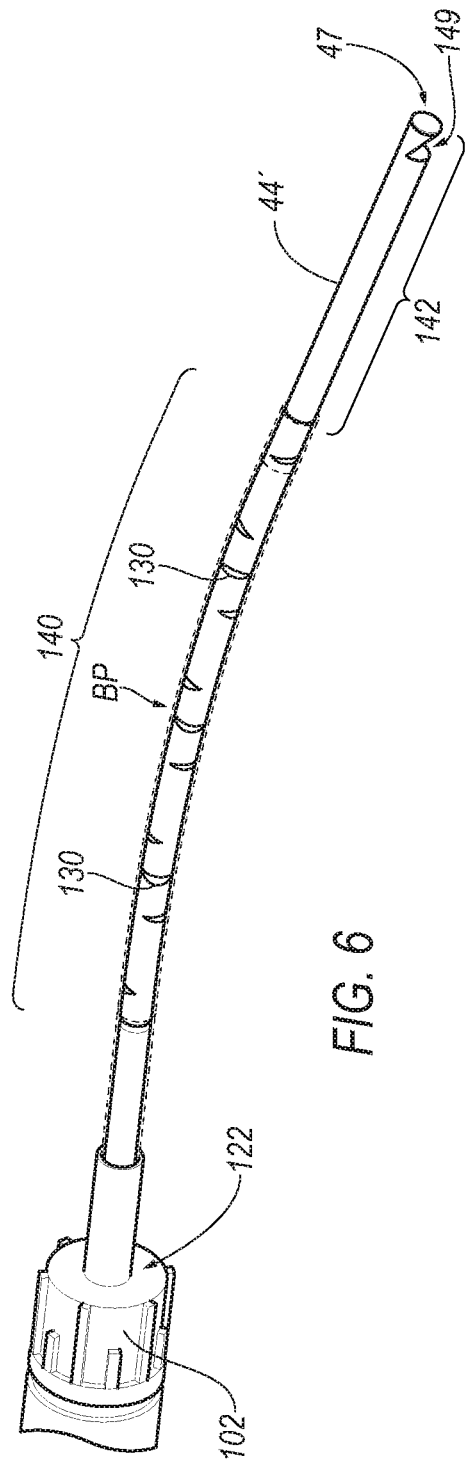
FIG. 6 is a partial perspective view of an inner and outer cannula assembly for a tissue cutting device.
Figure 7:
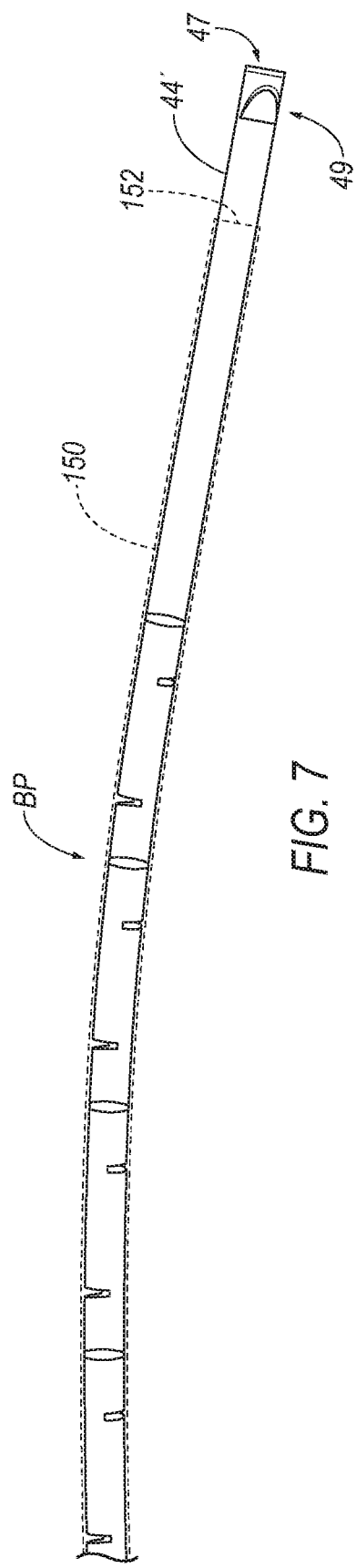
FIG. 7 is a side elevational view of the inner and outer cannula assembly of FIG. 6.

Referring to FIGS. 6-7, outer cannula 44' is shown. Outer cannula 44' is generally constructed similar to the outer cannula 44 described above, but further includes a relieved section 140 and an unrelieved section 142. The tissue opening 49 is positioned in the unrelieved section 142. In one exemplary arrangement, the relieved section 140 has a length that is slightly shorter than a length of the stiffening sleeve 104 (hidden in FIGS. 6 and 7). In a further exemplary arrangement, the relieved section 140 has a length that is greater than half the length of the outer cannula 44'. The relieving cuts 130 are disposed within the relieved section 140. The adjacent relieving cuts 130 are disposed approximately 90 degrees from one another, but are spaced along the length of the outer cannula 44', as is explained in further detail below.

Similar to outer cannula 44', inner cannula 50' is generally constructed similar to the inner cannula 50 described above, but further includes a relieved section (a portion of which is visible in FIGS. 8-9) 144 and an unrelieved section (not shown). The hinge 58, if provided, is positioned in the unrelieved section. In one exemplary arrangement, the relieved section 144 has a length that is slightly shorter than a length of the stiffening sleeve 104 (hidden in FIGS. 6 and 7). In a further exemplary arrangement, the relieved section 144 has a length that is greater than half the length of the inner cannula 50'. In yet a further exemplary arrangement, the relieved section 144 has a length that is the same as the length of the relieved section 140 of the outer cannula 44'. The relieving cuts 132 are disposed within the relieved section 144. The adjacent relieving cuts 132 are disposed 90 degrees from one another, but are spaced along the length of the inner cannula 50' so as to be offset from the relieving cuts 130 of the outer cannula 40'. More specifically, the relieving cuts 130 and 132 are offset from one another by approximately half the expected operational stroke length of the inner cannula 50'.

In operation, the inner cannula 50' is inserted into the outer cannula 44' similar to the arrangement discussed above in connection with FIGS. 5A-5B. The inner cannula 50' and the outer cannula 44' are mounted to the handpiece 40 such that they both rotate together to keep the tissue opening 49 aligned with the hinge 58. The inner cannula 50' and the outer cannula 44' are malleable such that they may be bent at a bend point BP to allow for ease of line of sight. To insure that the distal end 47 rotates the tissue opening 49 in plane, the relieving cuts 130/132 of the inner cannula 50' and the outer cannula 44' are offset from one another as discussed above. When the inner cannula 50' is in the cutting position (as shown in FIG. 8), the relieving cuts 130/132 opposite of each other and offset such that the relieving cuts 130/132 do not overlap with one another when the inner cannula 50' is in a reciprocating motion and to prevent binding from occurring when the inner cannula 50' and outer cannula 44' are rotated. When the inner cannula is in the retracted position (as shown in FIG. 9), the relieving cuts 130/132 are positioned 90 degrees from each other and also offset to allow for rotation without binding.

Relieving cuts 130/132 allow for vacuum to escape from the inner cannula 50' through the outer cannula 44'. To maintain vacuum through the device 40, a vacuum tubing 150 (FIG. 7) may be provided that seals off the relieving cuts 130 from communicating with the atmosphere. In one exemplary arrangement, the vacuum tubing 150 is formed as a heat shrink. In one exemplary arrangement, the vacuum tubing 150 has a length that extends distally past the relieving section 140, but proximally from the tissue opening 49. A distal end 152 seals against a portion of the unrelieved section 142 of the outer cannula 44'. In one exemplary arrangement, the vacuum tubing 150 may extend past the stiffening sleeve 104.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the disclosure should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A tissue cutting device, comprising:
   a handpiece;
   an outer cannula mounted for rotation with respect to the handpiece; and
   an inner cannula mounted for rotation with respect to the handpiece;
   wherein the outer cannula includes a plurality of outer relieving cuts disposed thereon;
   wherein the inner cannula includes a plurality of inner relieving cuts disposed thereon; and
   wherein the outer cannula is rotationally fixed with respect to the inner cannula such that the outer relieving cuts are maintained at a fixed angular offset from the inner relieving cuts during rotation of the inner cannula with respect to the handpiece.

2. The tissue cutting device of claim 1, wherein the outer cannula includes an outer relieved section and an outer unrelieved section, wherein the outer relieving cuts are disposed along the outer relieved section.

3. The tissue cutting device of claim 2, wherein the outer cannula is defined by a proximal end and a closed distal end, and a distal opening for receiving tissue is disposed adjacent the closed distal end within the outer unrelieved section.

4. The tissue cutting device of claim 3, wherein the outer relieved section extends from the proximal end to at least half the length of the outer cannula.

5. The tissue cutting device of claim 3, wherein the outer relieved section extends from the proximal end to over half the length of the outer cannula.

6. The tissue cutting device of claim 1, wherein the inner cannula includes an inner relieved section and an inner unrelieved section, wherein the inner relieving cuts are disposed along the inner relieved section.

7. The tissue cutting device of claim 6, wherein the inner cannula is defined by a proximal end and a distal end, and a hinge is disposed adjacent the distal end of the inner cannula within the inner unrelieved section.

8. The tissue cutting device of claim 7, wherein the inner relieved section extends from the proximal end to at least half the length of the inner cannula.

9. The tissue cutting device of claim 7, wherein the inner relieved section extends from the proximal end to over half the length of the inner cannula.

10. The tissue cutting device of claim 3, wherein the inner cannula is mounted for reciprocating movement within the outer cannula between a first position and a second position to sever tissue disposed in the distal opening of the outer cannula.

11. The tissue cutting device of claim 10, wherein when the inner cannula is in the first position, a distal end of the inner cannula is positioned proximally of the distal opening formed in the outer cannula.

12. The tissue cutting device of claim 10, wherein the inner cannula is defined by a proximal end and a distal end, and the inner cannula and the outer cannula are bent about a bend point such that the distal ends of the inner cannula and the outer cannula are positioned along an axis that is different than an axis upon which the proximal ends of the inner cannula and the outer cannula are positioned on.

13. The tissue cutting device of claim 1, wherein each of the outer and inner relieving cuts have a diamond shape when viewed in plane.

14. The tissue cutting device of claim 1, further comprising a vacuum sleeve disposed over the outer relieving cuts of the outer cannula and configured to seal off the outer receiving cuts of the outer cannula to atmosphere.

15. The tissue cutting device of claim 2, further comprising a vacuum sleeve disposed over the outer relieving cuts of the outer cannula and configured to seal off the outer receiving cuts of the outer cannula to atmosphere, wherein the vacuum sleeve has a distal end sealed to the outer unrelieved section of the outer cannula.

16. The tissue cutting device of claim 1, further comprising a stiffening sleeve that is positioned over the outer cannula.

17. The tissue cutting device of claim 16, wherein the stiffening sleeve is connected to a hub, and wherein the hub connects to the handpiece.

18. The tissue cutting device of claim 17, wherein the stiffening sleeve is malleable.

19. The tissue cutting device of claim 10, wherein the outer relieving cuts are offset from the inner relieving cuts in the longitudinal and the angular directions such that the inner relieving cuts do not overlap with the outer relieving cuts when the inner cannula is in the first position and the second position.

20. The tissue cutting device of claim 10, wherein the inner relieving cuts are offset from the outer relieving cuts in the longitudinal and the angular directions such the inner relieving cuts do not overlap with the outer relieving cuts during the reciprocating movement of the inner cannula within the outer cannula between the first position and the second position to server tissue.

\* \* \* \* \*